(12) United States Patent　　(10) Patent No.:　US 12,560,495 B2

Cooper　　(45) Date of Patent:　Feb. 24, 2026

(54) TEMPERATURE SENSOR DEVICES AND METHODS FOR THE USE THEREOF

(71) Applicant: Tommy Gene Cooper, Friendswood, TX (US)

(72) Inventor: Tommy Gene Cooper, Friendswood, TX (US)

( * ) Notice: Subject to any disclaimer, the term of this patent is extended or adjusted under 35 U.S.C. 154(b) by 1058 days.

(21) Appl. No.: 17/665,071

(22) Filed: Feb. 4, 2022

(65) Prior Publication Data

US 2022/0252467 A1　Aug. 11, 2022

Related U.S. Application Data

(60) Provisional application No. 63/146,168, filed on Feb. 5, 2021.

(51) Int. Cl.

| | |
|---|---|
| *G01K 7/22* | (2006.01) |
| *A61B 5/00* | (2006.01) |
| *A61G 11/00* | (2006.01) |
| *G01K 7/02* | (2021.01) |
| *G01K 13/20* | (2021.01) |

(52) U.S. Cl.

CPC ............ *G01K 13/20* (2021.01); *A61B 5/6832* (2013.01); *A61G 11/00* (2013.01); *G01K 7/02* (2013.01); *G01K 7/22* (2013.01); *A61B 2560/0214* (2013.01); *A61B 2562/0271* (2013.01); *A61G 2203/46* (2013.01)

(58) Field of Classification Search

None

See application file for complete search history.

(56) References Cited

U.S. PATENT DOCUMENTS

| | | | |
|---|---|---|---|
| 6,398,727 B1 | 6/2002 | Bui et al. | |
| 6,830,549 B2 | 12/2004 | Bui et al. | |
| 2012/0289855 A1* | 11/2012 | Bieberich | .............. G01K 13/20 |
| | | | 600/549 |
| 2018/0028069 A1* | 2/2018 | Shi | ........................... G01K 1/14 |

(Continued)

FOREIGN PATENT DOCUMENTS

| | | | |
|---|---|---|---|
| CN | 103948375 A | * | 7/2014 |
| CN | 105973301 A | * | 9/2016 |

OTHER PUBLICATIONS

English Translation CN 105973301 A, You Lirong Zheng Yongming, 6 pages, printed Apr. 18, 2025, (Year: 2016).*

(Continued)

*Primary Examiner* — Alex M Valvis

(74) *Attorney, Agent, or Firm* — William R. Childs; Childs Patent Law PLLC

(57)　　　ABSTRACT

The present disclosure relates to temperature sensor devices for measuring the internal body temperature of a patient, as well as methods of using the same. A benefit to the temperature sensor devices can be providing for the accurate and continuous measurement and monitoring of the internal body temperature of a patient. Another benefit to the temperature sensor devices can be providing an ability to measure and monitor the internal body temperature of a patient in a hygienic and safe manner. Additional benefits to the temperature sensor devices can be providing power efficient, cost effective, compact, and convenient devices for measuring the internal body temperature of a patient.

17 Claims, 5 Drawing Sheets

(56)         References Cited

U.S. PATENT DOCUMENTS

| | | | | |
|---|---|---|---|---|
| 2018/0184902 A1* | 7/2018 | Meyerson | ................ | A61B 5/01 |
| 2019/0046033 A1* | 2/2019 | Gannon | ................ | G01K 1/024 |
| 2020/0217727 A1* | 7/2020 | Heitz | .................... | G01K 13/20 |
| 2020/0271824 A1* | 8/2020 | Shimuta | ............... | A61B 5/6832 |
| 2022/0101992 A1* | 3/2022 | Porter | ..................... | A61B 5/01 |

OTHER PUBLICATIONS

English Translation CN 103948375 A, Huang Yuxin Huang Lian Qiao Qiao Shuang, 8 pages, printed Apr. 18, 2025, (Year: 2014).*
Ball, et al. Biomedicine The European Journal of Clinical and Biological Research, "A Clinical Apraisal of Transcutaneous Deep Body Temperature," University Department of Medicine, Biomedicine, 1973, Issue No. 4, vol. 17, 7 pages.
Fox, et al., "A New Method for Monitoring Deep Body Temperature From the Skin Surface," National Institute of Medical Research, Clin Sci Mol Med (1973) 44 (1): 81-86.

* cited by examiner

300

302

304

314

324

306

312

308    310

322

318

320

316

400

402

400

418

420

422

412

414

416

410

404 406 408

TEMPERATURE SENSOR DEVICES AND METHODS FOR THE USE THEREOF

CROSS-REFERENCE TO RELATED APPLICATIONS

This U.S. Patent Application claims priority to U.S. Provisional Application No. 63/146,168, filed on Feb. 5, 2021, which is incorporated herein in its entirety.

TECHNICAL FIELD

The present disclosure relates to temperature sensor devices for measuring the internal body temperature of a patient, as well as methods of using the same. A benefit of the temperature sensor devices can be providing for the accurate and continuous measurement and monitoring of the internal body temperature of a patient. Another benefit of the temperature sensor devices can be providing an ability to measure and monitor the internal body temperature of a patient in a hygienic and safe manner. Additional benefits of the temperature sensor devices can be providing power efficient, cost effective, compact, and convenient devices for measuring the internal body temperature of a patient.

BACKGROUND

Internal or core body temperature is a vital sign of the state of health of the body, including the internal body organs and tissues. Temperature monitoring is also important for detecting the presence of infections or other diseases, and for tracking progress during patient treatment. During surgery, temperature monitoring is important for detection of hypothermia and is used by medical staff to regulate warming devices. Internal body temperature is generally measured by using traditional thermometers or other types of probes. While traditional temperature measurement methods can be highly accurate, they may also be difficult to perform on newborns, and may add to the risk of infection in infants, as well as patients and healthcare providers. Traditional methods also require regular repetition of temperature measurements in order to monitor temperature over time, further adding to the risk of infection to patients and healthcare personnel. Accordingly, in various patient and healthcare settings, wearable devices making use of skin sensors are often used for monitoring a patient's internal body temperature. The use of temperature sensor devices worn on the skin is of particular importance in the care of infant patients in need of thermal regulation in an incubator or isolette. Internal body temperature can be estimated from the skin temperature; however, skin temperature may not correlate well to the internal temperature of the patient.

There is a need for temperature sensor devices that can accurately measure the internal body temperature of a patient, while providing for continuous internal temperature monitoring. There is a need for temperature sensor devices that can measure the internal body temperature of a patient in a hygienic and safe manner, especially during a COVID-19 pandemic. There is a need for temperature sensor devices that can provide power efficient, cost effective, compact, and convenient devices for measuring the internal body temperature of a patient.

SUMMARY

Embodiments herein are directed to temperature sensor devices, and methods for the use thereof.

In an aspect, a temperature sensor device for measuring the internal body temperature of a patient includes: a gel skin adhesive layer, an electrically insulating layer, a skin-side thermally insulating layer, a sensor assembly, a thermally conductive layer, and an upper thermally insulating layer; wherein the gel skin adhesive layer is in direct contact with at least a portion of the electrically insulating layer; wherein the electrically insulating layer is in direct contact with at least a portion of the skin-side thermally insulating layer; wherein the sensor assembly comprises at least one skin temperature sensor located on a skin-facing exterior of the sensor assembly; wherein the sensor assembly comprises a thin film heater and a heater temperature sensor separated from at least one skin temperature sensor by the thermally conducting layer; and wherein the skin-side thermally insulating layer connects to the upper thermally insulating layer, surrounding the sensor assembly. In an embodiment, at least one skin sensor is positioned in contact with the skin-side thermally insulating layer. In certain embodiments, the temperature sensor device further comprises a medial thermally insulating layer in direct contact with at least a portion of the skin-side thermally insulating layer and the upper thermally insulating layer.

In certain embodiments, the sensor assembly further comprises a first printed circuit board and a second printed circuit board; wherein at least one skin temperature sensor is electrically connected and mounted on a skin-side of the first printed circuit board; wherein the thin film heater and the heater temperature sensor are electrically connected to and mounted on the second printed circuit board; wherein the first printed circuit board is connected to the second printed circuit board and the thermally conductive layer is positioned between at least a portion of the first printed circuit board and at least a portion of the second printed circuit board.

In various embodiments, the gel skin adhesive layer comprises a hydrogel material, a silicone gel material, or a combination thereof. In certain embodiments, at least one of the first the first printed circuit board and the second printed circuit board are made of a flexible material.

In certain embodiments, the at least one skin sensor comprises a first skin sensor and a second skin sensor, and the first skin sensor is a thermistor. In certain embodiments, the heater temperature sensor comprises a thermocouple, a thermistor, a solid-state sensor configured to measure temperatures from about 32° C. to about 41° C., or a combination thereof.

In some embodiments, the sensor assembly further comprises a third printed circuit board and a control circuit electrically connected to and mounted on the third printed circuit board, and wherein the control circuit is configured to control the temperature of the thin film heater by generating a control signal that is proportionate to a difference between a skin temperature measured by the at least one skin temperature sensor and the heater sensor. In certain embodiments, the third printed circuit board is connected to the second printed board and an interior insulating foam layer is located between at least a portion of the third printed board and a portion of the second printed board.

In certain embodiments, the sensor assembly has a thickness of from about 2.0 mm to about 4.0 mm and a longest length measurement of from about 1.0 cm to about 2.0 cm. In certain embodiments, the thin film heater has a thickness of from about 0.2 mm to about 0.4 mm and a longest length measurement of from about 1.0 cm to about 2.0 cm. In certain embodiments, the thermally conducting layer has a thickness of from about 0.5 mm to about 1.0 mm and a longest length measurement of from about 1.0 cm to about 2.0 cm. In some embodiments, the skin-side thermally insulating, and the upper thermally insulating layer form an insulating sheath having a thickness of from about 4.0 mm to about 7.0 mm and a longest length measurement of from about 2.0 cm to about 5.0 cm.

In certain embodiments, the temperature sensor device further includes a cable electrically connected to the sensor assembly at a distal end of the cable and to a connector at a proximal end of the cable. In certain embodiments, the cable has a thickness of from about 0.5 mm to about 1.0 mm, a width of from about 4.0 mm to about 6.0 mm, and a length of from about 80.0 cm to about 100.0 cm. In some embodiments, the temperature sensor device further includes a cable electrically connected to the sensor assembly at a distal end of the cable and to a connector at a proximal end of the cable, wherein the cable is substantially round with a diameter of about 1.5 to 3.0 mm.

In certain embodiments, the temperature sensor device further includes a battery module disposed in line with the cable. In some embodiments, the battery module includes a temperature control circuit electrically connected to the sensor assembly, and the battery module is electronically connected to a battery contained within the battery module. In certain embodiments, the battery module has a diameter of from about 2.0 cm to about 4.0 cm and a thickness of from about 4.0 mm to about 8.0 mm.

In some embodiments, the cable has a length of from about 5.0 cm to about 10.0 cm between the connector and the battery module, and a length of from about 80.0 cm to about 100.0 cm between the battery module and the sensor assembly.

In certain embodiments, the connector is a 2 to 21-pin connector, the battery is a lithium battery, and the temperature control circuit is a microcontroller or a servo controller.

In certain embodiments, the first skin sensor and the second skin sensor are monitored by at least one microcontroller configured to detect a failure in the first skin sensor or the second skin sensor, wherein the microcontroller is configured to send an end of life signal to a monitor if the failure is detected.

In some aspects, a battery voltage is monitored by at least one microcontroller configured to detect a battery cutoff voltage of from about 2.2 volts to about 2.5 volts or less, and wherein the microcontroller is configured to send an end of life signal to a monitor if the battery cutoff voltage is detected.

In certain embodiments, the sensor device has a power usage of from about 2 mW to about 10 mW.

The present disclosure provides methods for measuring the internal body temperature of a patient. In some embodiments, such a method includes: connecting a temperature sensor device to a skin area of the patient, connecting the temperature sensor device to an incubator, and monitoring the internal body temperature of the patient for a duration; wherein the temperature sensor device comprises a gel skin adhesive layer, an electrically insulating layer, a skin-side thermally insulating layer, a sensor assembly, a thermally conductive layer, and an upper thermally insulating layer; wherein the gel skin adhesive layer is in direct contact with at least a portion of the electrically insulating layer; wherein the electrically insulating layer is in direct contact with at least a portion of the skin-side thermally insulating layer; wherein the sensor assembly comprises at least one skin temperature sensor located on a skin-facing exterior of the sensor assembly; wherein the sensor assembly comprises a thin film heater and a heater temperature sensor separated from the at least one skin temperature sensor by the thermally conducting layer; and wherein the skin-side thermally insulating layer connects to the upper thermally insulating layer, surrounding the sensor assembly.

In certain embodiments, the method further includes detaching and re-attaching the sensor device to the skin area of the same patient from 1 to about 5 times before disposing of the sensor device. In certain embodiments, the patient is an infant or a surgical patient.

BRIEF DESCRIPTION OF THE DRAWINGS

The foregoing summary, as well as the following detailed description of the embodiments, will be better understood when read in conjunction with the attached drawings. For the purpose of illustration, there are shown in the drawings some embodiments, which may be preferable. It should be understood that the embodiments depicted are not limited to the precise details shown. Unless otherwise noted, the drawings are not to scale.

DETAILED DESCRIPTION

Unless otherwise noted, all measurements are in standard metric units.

Unless otherwise noted, all instances of the words "a," "an," or "the" can refer to one or more than one of the word that they modify.

Unless otherwise noted, the phrase "at least one of" means one or more than one of an object. For example, "at least one of a single walled carbon nanotube, a double walled carbon nanotube, and a triple walled carbon nanotube" means a single walled carbon nanotube, a double walled carbon nanotube, or a triple walled carbon nanotube, or any combination thereof.

Unless otherwise noted, the term "about" refers to ±10% of the non-percentage number that is described. For example, about 2 mm, would include 1.8 to 2.2 mm. Unless otherwise noted, the term "about" refers to ±5% of a percentage number. For example, about 20% would include 15 to 25%. When the term "about" is discussed in terms of a range, then the term refers to the appropriate amount less than the lower limit and more than the upper limit. For example, from about 80 to about 100 cm would include from 72 to 110 cm.

Unless otherwise noted, properties (height, width, length, ratio etc.) as described herein are understood to be averaged measurements.

Unless otherwise noted, the temperature control is used as a reference point, such that the terms "proximal" and "distal," as used herein, refer to the relative proximity of an object or a portion of an object to the temperature control.

Unless otherwise noted, the terms "provide", "provided" or "providing" refer to the supply, production, purchase, manufacture, assembly, formation, selection, configuration, conversion, introduction, addition, or incorporation of any element, amount, component, reagent, quantity, measurement, or analysis of any method or system of any embodiment herein.

Embodiments of Temperature Sensor Devices

Figures 1, 2:
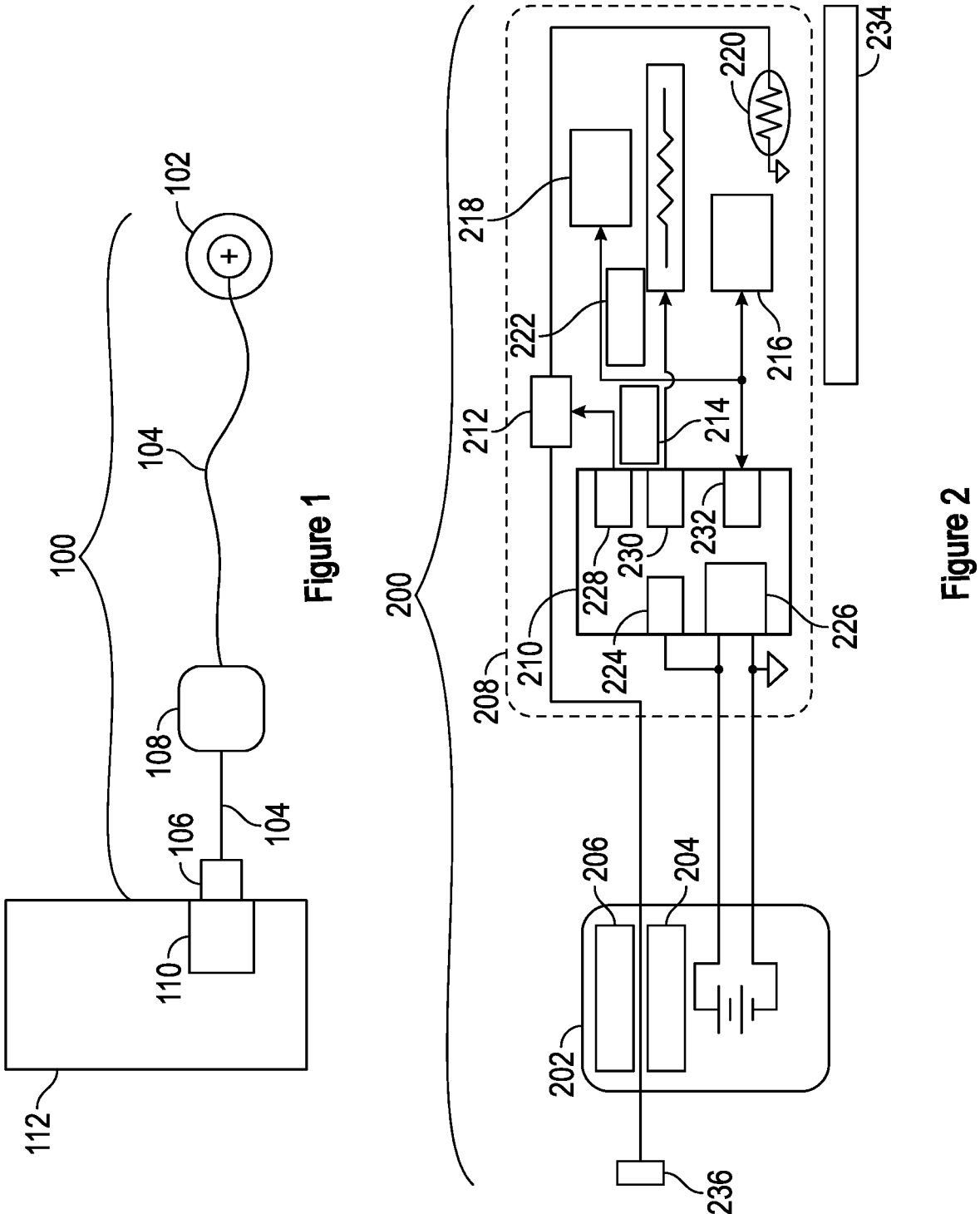
FIG. 1 shows an overall schematic illustration of a temperature sensor device according to embodiments disclosed herein.
FIG. 2 shows a schematic illustration including a circuit diagram according to embodiments of a temperature sensor device disclosed herein.

An embodiment of a temperature sensor device as disclosed herein is shown in FIG. 1. Temperature sensor device 100 includes sensor assembly 102, cable 104 electrically connected to sensor assembly 102 at a distal end of cable 104 and to connector 106 at a proximal end of cable 104; and battery module 108 disposed in line with cable 104. Connector 106 is connected to incubator temperature control 110 of incubator 112.

An embodiment of a temperature sensor device as disclosed herein is shown in FIG. 2. Temperature sensor device 200 includes patient warmer connector 236, battery module 202 including battery 204 and wire 206; and sensor assembly 208 including temperature control circuit 210, transistor switch 212, first temperature sensor 216, second temperature sensor 218, skin temperature sensor 220, and heater 222. Transistor switch 212 is electrically connected to patient warmer connector 236 through battery module 202 using wire 206 and to skin temperature sensor 220. Temperature control circuit 210 includes analog/digital converter 224 and power connection 226 electrically connected to battery 204; digital output 228 electrically connected to transistor switch 212; pulse width modulator 230 electrically connected to heater 222; and 12C serial port 232 electrically connected to first temperature sensor 216 and to second temperature sensor 218. Temperature sensor device 200 is connected to patient skin area 234 by connection with sensor assembly 208, and electrically connected to patient warmer through patient warmer connector 236.

Figure 3A:
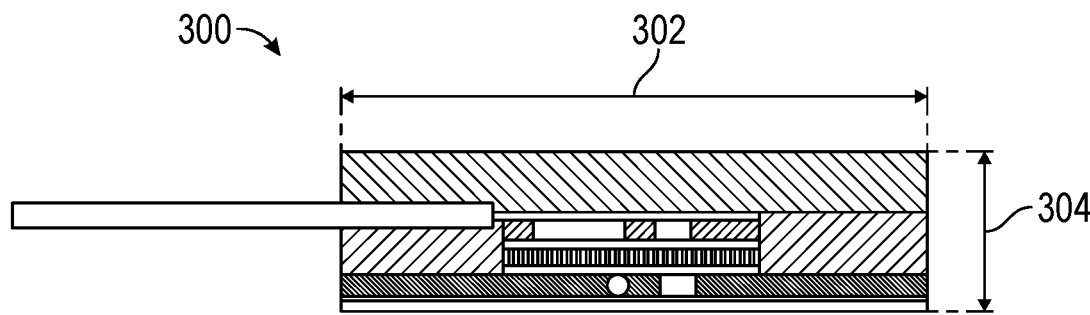
FIG. 3A shows a schematic illustration of a cutaway side view of a sensor assembly according to embodiments of a temperature sensor device disclosed herein.
Figure 3B:
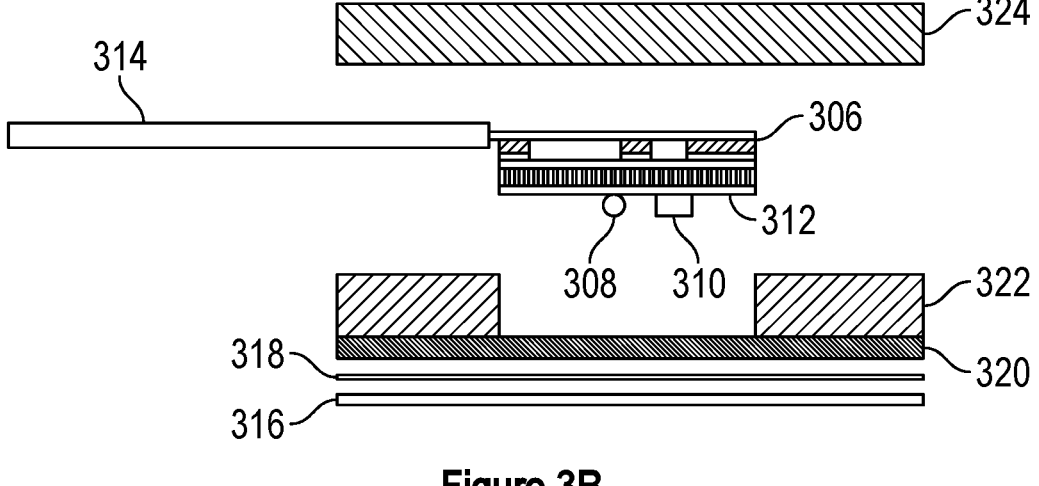
FIG. 3B shows a schematic illustration of an expanded cutaway side view of a sensor assembly according to embodiments of a temperature sensor device disclosed herein.

An embodiment of a temperature sensor device as disclosed herein is shown in FIGS. 3A and 3B. Assembly 300 in FIG. 3A has a longest length measurement 302 and thickness 304. FIG. 3B shows a separated view of FIG. 3A, including skin temperature sensors 308 and 310 located on skin-facing exterior 312 of sensor assembly 306; cable 314 electrically connected to sensor assembly 306; gel skin adhesive layer 316; electrically insulating layer 318; skin-side thermally insulating layer 320 having cut outs 321 and 323 to allow skin temperature sensors 308 and 310 to contact electrically insulating layer 318; medial thermally insulating layer 322; and upper thermally insulating layer 324.

Figure 4A:
FIG. 4A shows a schematic illustration of a cutaway side view of a sensor assembly according to embodiments of a temperature sensor device disclosed herein.
Figure 4B:
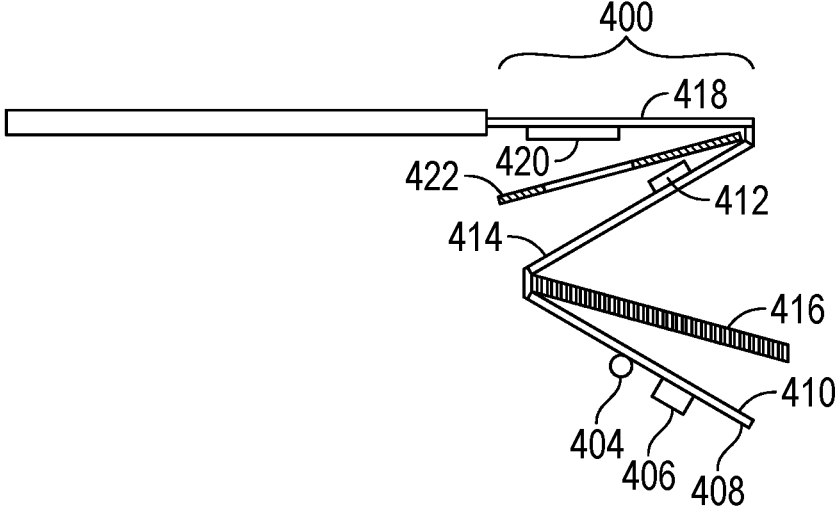
FIG. 4B shows a schematic illustration of an expanded cutaway side view of a sensor assembly according to embodiments of a temperature sensor device disclosed herein.
Figure 4C:
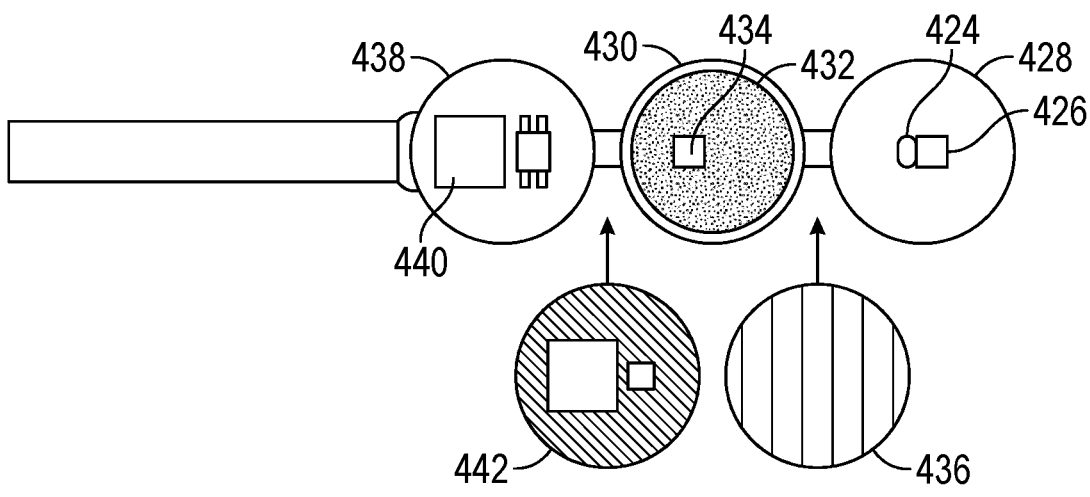
FIG. 4C shows a schematic illustration of an expanded top view of a sensor assembly according to embodiments of a temperature sensor device disclosed herein.

An embodiment of a sensor assembly as disclosed herein is shown in FIGS. 4A, 4B, and 4C. FIG. 4A shows a side cutaway view of sensor assembly 400 electrically connected to cable 402. FIG. 4B shows an expanded view of the sensor assembly in FIG. 4A, including skin temperature sensors 404 and 406 mounted on skin-facing exterior 408 of first printed circuit board 410; second printed circuit board 414 having a thin film heater and heater temperature sensor 412 mounted thereon and separated from skin temperature sensors 404 and 406 by thermally conducting layer 416; third printed circuit board 418 having control circuit 420 mounted thereon; and interior insulating foam layer 422 located between second printed circuit board 414 and third printed circuit board 418. FIG. 4C shows an expanded top view of the sensor assembly shown in FIG. 4A, including skin temperature sensors 424 and 426 electrically connected to and mounted on a skin side of first printed circuit board 428; second printed circuit board 430 having thin film heater 432 and heater temperature sensor 434 electrically connected to and mounted thereon, and being connected to first printed circuit board 428; thermally conductive layer 436 positioned between first printed circuit board 428 and second printed circuit board 430; third printed circuit board 438 having control circuit 440 electrically connected to and mounted thereon, and being connected to second printed circuit board 430; and insulating foam layer 442 positioned between second printed circuit board 430 and third printed circuit board 438.

Traditional methods of measuring internal body temperature typically use thermometers that measure body temperature in any of several locations in the body, including most commonly the mouth, ear, armpit, and rectum. Many thermometers are made to directly contact the body to measure body temperature, while others, such as infrared thermometers, use a lens to focus infrared light emitting from a body surface onto a thermopile detector, in order to measure the body surface temperature without contacting the body.

Measurement and monitoring of body temperature is centrally important in healthcare and clinical settings. There is often a need to repeatedly measure and monitor the internal body temperature of patients in order to determine the status of the patients' health, and to correctly diagnose or treat infection or disease over the course of patient care. An important application of internal temperature monitoring is during the care of premature infants in need of thermal regulation in an incubator or isolette.

Traditional thermometers may not be practical for many healthcare and clinical applications requiring internal body temperature monitoring. The need for repeated measurements can be impractical, increases changes for spreading infection, and can be disruptive for healthcare personnel as well as patients. The small size of infants can also make it difficult to effectively measure their core temperatures using traditional methods. To address these difficulties, wearable devices making use of skin sensors are often used to monitor a patient's internal body temperature over time. The use of skin sensors is especially important for the care of infant patients in need of thermal regulation. The use of skin sensors can also help to prevent the spread of infection between healthcare providers and patients, by reducing the need for repeated direct patient contact.

While technological improvements have been made to skin surface temperature measurement devices, significant challenges remain. Internal body temperature can be estimated from the temperature of the skin surface; however, skin temperature may not correlate well to the internal body temperature. Loss of heat from the skin to the ambient air can have a significant effect on the accuracy of skin temperature sensor measurements as well. This difficulty has been partly addressed by surrounding skin sensors with layers of insulating materials to avoid heat loss. The insulating layer may introduce another potential risk factor for the transfer of infection, especially if the insulating layer is removed and reattached multiple times.

Also, the skin temperature correlation to internal body temperature is affected by the physiological responses to core temperature changes. When the core temperature is lower the body may respond with vasoconstriction which reduces capillary blood flow to the skin to reduce heat loss. When core temperature is increased, the body may respond with vasodilation, which increases blood flow, and with sweating to remove heat. These physiological responses affect the skin temperature. By creating an area of zero heat loss, embodiments of temperature sensors herein can bring deep body temperature to the skin surface, where it is measured by the skin temperature sensor.

Indeed, another challenge encountered with the use of wearable skin temperature sensor devices is the risk of transferring infections to patients and their healthcare providers. While the use of skin sensors to monitor body temperature can reduce the potential for infection transmission by reducing the frequency of patient contact, conventional skin temperature sensors are routinely re-used between patients. Some such sensors are equipped with removable sensor covers with adhesive pads, which can be changed between patients while the sensor is re-used. While this may help to reduce costs, it does increase the risk that an infection will be transferred from one patient to another, or between a patient and a healthcare provider.

Some conventional skin temperature sensor devices are configured to connect to an infant incubator or isolette, to allow monitoring of the body temperature of infants placed in an incubator for thermal regulation. Such devices typically use the incubator power source, so that the sensor's functioning is dependent on the incubator. Conventional sensor devices are also typically programmed using the incubator's control mechanisms, adding another degree of dependency on the correct functioning of the incubator. Consequently, an infant's temperature cannot be continuously monitored during any time that the infant needs to be moved from the incubator, such as for washing or other treatment. A malfunction of the incubator may also cause the sensor to stop working correctly.

Embodiments of temperature sensor devices disclosed herein can provide solutions for the challenges posed by conventional skin temperature sensor devices. Embodiments of temperature sensor devices herein can provide for the accurate measurement of internal body temperature when worn on the skin. One benefit of embodiments herein can be providing a sensor that can evoke a physiological response in the patient that results in bringing the internal body temperature to the skin surface. Another benefit can be providing sensor devices that can create a region of effectively zero heat flow from the skin to the ambient air. Embodiments of devices herein can provide benefits of measuring and monitoring the internal body temperature of a patient in a way that is allows continuous, real-time monitoring while being more hygienic and thus safer for the patient and medical personnel, as well as being more comfortable than conventional sensors. Embodiments of sensor devices herein can also provide the benefits of more power efficient, cost effective, compact, and convenient devices for measuring the internal body temperature of a patient.

Embodiments herein are directed to temperature sensor devices. In an aspect, a temperature sensor device for measuring the internal body temperature of a patient includes: a gel skin adhesive layer, an electrically insulating layer, a skin-side thermally insulating layer, a sensor assembly, a thermally conductive layer, and an upper thermally insulating layer; wherein the gel skin adhesive layer is in direct contact with at least a portion of the electrically insulating layer; wherein the electrically insulating layer is in direct contact with at least a portion of the skin-side thermally insulating layer; wherein the sensor assembly comprises at least one skin temperature sensor located on a skin-facing exterior of the sensor assembly; wherein the sensor assembly comprises a thin film heater and a heater temperature sensor separated from at least one skin temperature sensor by the thermally conducting layer; and wherein the skin-side thermally insulating layer connects to the upper thermally insulating layer, surrounding the sensor assembly. In an embodiment, the at least one skin sensor is positioned in contact with the skin-side thermally insulating layer.

In certain embodiments, the gel skin adhesive layer includes a silicone gel adhesive layer; in some embodiments, the gel skin adhesive layer includes a hydrogel material, a silicone gel material, or a combination thereof. In such embodiments, the gel skin adhesive layer can have a benefit of an adhesive layer of sufficient strength that can effectively hold the sensor assembly in place on the skin of a patient. Such embodiments can have a benefit of allowing the sensor assembly to be removed and replaced onto the same or a different position on the skin of a patient up to several times.

The electrically insulating layer in some embodiments includes an electrically insulating film. In certain embodiments, the electrically insulating layer includes a single-side adhesive film. In certain embodiments, the single-side adhesive film can be positioned on an upper surface of the electrically insulating film opposite to the silicone gel adhesive layer; in such embodiments, the single-side adhesive film can adhere the electrically insulating film to the skin-side thermally insulating layer. The electrically insulating layer can have a benefit of separating the skin temperature sensor from direct contact with the skin of a patient, thus providing an electrical isolation for the skin temperature sensors and protecting the patient. The electrically insulating layer can also have a benefit of providing a moisture seal to protect the operation of the skin temperature sensor.

The skin-side thermally insulating layer in certain embodiments includes an insulating closed cell foam material. In certain embodiments, at least one skin temperature sensor is in direct contact with at least a portion of the skin-side thermally insulating layer. In certain embodiments, the skin-side thermally insulating layer has at least one cut-out allowing the at least one skin temperature sensor to be in direct contact with at least a portion of the electrically insulating layer. Such embodiments can have a benefit of reducing thermal insulating barriers between the at least one skin temperature sensor and the skin of the patients; such embodiments can have a benefit of increasing the accuracy of the temperature sensor device by providing better thermal contact of the at least one skin temperature sensor with the skin of the patient.

In certain embodiments, the skin-side thermally insulating layer includes a single-side adhesive film on an upper surface; in such embodiments, the single-side adhesive film can adhere at least a portion of the skin-side thermally insulating layer to the upper thermally insulating layer. Such embodiments can have a benefit of providing thermal insulation for the sensor assembly, as well as a benefit of a seal against moisture intrusion. In other embodiments, the temperature sensor device further includes a medial thermally insulating layer in direct contact with at least a portion of the skin-side thermally insulating layer. In such embodiments, the medial thermally insulating layer includes a closed cell foam material. In certain embodiments, the medial thermally insulating layer includes a single-side adhesive film on an upper surface; in such embodiments, the single-side adhesive film can adhere at least a portion of the medial thermally insulating layer to the upper thermally insulating layer. In such embodiments, the medial thermally insulating layer includes a cut-out that allows the sensor assembly to be in direct contact with at least a portion of the skin-side thermally insulating layer. Such embodiments can provide a benefit of layers of insulating material that surround the sensor assembly to provide effective thermal insulation for the sensor assembly and a moisture seal.

The upper thermally insulating layer in various embodiments can include an insulating closed cell foam material. In certain embodiments, the upper thermally insulating layer includes a single-side adhesive film on a lower surface; in such embodiments, the single-side adhesive film can adhere the upper thermally insulating layer to at least a portion of the skin-side thermally adhesive layer; in other embodiments, the single-side adhesive film can adhere the upper thermally insulating layer to at least a portion of the medial thermally adhesive layer. In certain embodiments, the single-side adhesive film adheres the upper thermally insulating layer to at least a portion of the sensor assembly. Such embodiments can provide a benefit of an effective thermal insulation for the sensor assembly, as well as an effective moisture seal.

Certain embodiments include a cable electrically connected to the sensor assembly at a distal end of the cable. In certain embodiments, the cable is in contact with at least a portion of the upper thermally insulating layer and the skin-side thermally insulating layer; in other embodiments, the cable is in contact with at least a portion of the upper thermally insulating layer and the medial thermally insulating layer. In certain embodiments, the single-side adhesive films of the contacting thermally insulating layers can adhere to a portion of the distal end of the cable. Such embodiments can have a benefit of forming a thermally insulating seal surrounding the sensor assembly and a distal end portion of the cable, as well as providing an effective moisture barrier for the sensor assembly. Such embodiments can also provide a benefit of a temperature sensor device that is advantageous for single patient use; such embodiments can also provide a benefit of being disposable after single patient use.

Various embodiments of a temperature sensor device include a sensor assembly. In such embodiments, the sensor assembly includes at least one skin temperature sensor located on a skin-facing exterior of the sensor assembly. In certain embodiments, the at least one skin sensor comprises a first skin sensor and a second skin sensor. Embodiments including a first skin temperature sensor and a second skin temperature sensor can provide a benefit of greater accuracy for the temperature sensor device. Another benefit can be the separation of the sensor for an infant incubator from the temperature controller for the current sensor, thus minimizing any interference with the incubator temperature measurement. In certain such embodiments, the first skin sensor is a thermistor, which can provide a benefit of a separate thermistor that allows for using independent temperature sensors for the temperature sensor device. Such embodiments can have a benefit of avoiding errors in performance of the temperature sensor device performance, because the thermistor may not be the same for every incubator, and the excitation current may not be the same for every incubator; detecting the resulting voltage across the thermistor going to the incubator may be complicated, and any errors would affect the performance of the device.

In certain embodiments, the sensor assembly includes a thin film heater and a heater temperature sensor separated from the at least one skin temperature sensor by a thermally conductive layer. In such embodiments, the thermally conductive layer allows the thin film heater to warm the area above the thermally insulating layer. Such embodiments can provide a benefit of providing a measured skin temperature that correlates accurately with the internal body temperature. In such embodiments, the at least one skin temperature sensor can evoke a physiological response in the patient that results in bringing the internal body temperature to the skin surface. In such embodiments, the sensor assembly creates a region where there is zero heat flow from the skin to the ambient air; the skin temperature in this zero-heat loss region correlates with the internal body temperature. Such embodiments can provide an advantage of greater accuracy in measurement of internal body temperature compared to the current standard skin temperature sensors, which are subject to significant errors due to capillary vasoconstriction responses to cold air, reduced blood flow to the extremities, general poor thermal regulation in newborn infants, and other factors. In certain embodiments, the heater temperature sensor includes a thermocouple, a thermistor, a solid-state sensor configured to measure temperatures from about 32° C. to about 41° C., or a combination thereof.

In certain embodiments, the sensor assembly further includes a first printed circuit board and a second printed circuit board. In such embodiments, at least one skin temperature sensor is electrically connected and mounted on a skin-side of the first printed circuit board, and the thin film heater and the heater temperature sensor are electrically connected to and mounted on the second printed circuit board. In such embodiments, the first printed circuit board is connected to the second printed circuit board, and the thermally conductive layer is positioned between at least a portion of the first printed circuit board and at least a portion of the second printed circuit board. In certain embodiments, at least one of the first the first printed circuit board and the second printed circuit board are made of a flexible material. Such embodiments can provide benefits of a cost-effective sensor assembly, and a compact size for the sensor assembly that is comfortable and convenient for patient use.

In certain embodiments, the at least one skin temperature sensor is soldered to the skin-side of the first printed circuit board. In certain embodiments, the at least one skin temperature sensor includes at least one sensor having an electrically insulated package and insulated wires, wherein the insulated wires are soldered to an upper surface of the first printed circuit board through holes in the first printed circuit board; in such embodiments, the insulated sensors can directly contact at least a portion of the gel skin adhesive layer.

In some embodiments, the sensor assembly further includes a third printed circuit board and a control circuit electrically connected to and mounted on the third printed circuit board, and wherein the control circuit is configured to control the temperature of the thin film heater by generating a control signal that is proportionate to a difference between a skin temperature measured by the at least one skin temperature sensor and the heater sensor. In certain embodiments, the third printed circuit board is connected to the second printed board and an interior insulating foam layer is located between at least a portion of the third printed board and a portion of the second printed board. Such embodiments can provide a benefit of providing a control circuit for the sensor assembly that is separate from the control circuitry of an infant incubator. Such embodiments can thus provide benefits of a temperature sensor device that is advantageous for single-patient use, and disposable after single patient use.

In certain embodiments, the sensor assembly has a thickness of from about 2.0 mm to about 4.0 mm and a longest length measurement of from about 1.0 cm to about 2.0 cm. In certain embodiments, the sensor assembly has a thickness of from about 2.4 mm to about 3.6 mm and a longest length measurement of from about 1.2 cm to about 1.8 cm. In certain embodiments, the sensor assembly has a thickness of from about 2.8 mm to about 3.2 mm and a longest length measurement of from about 1.4 cm to about 1.6 cm. Such embodiments can provide a benefit of a temperature sensor device that is compact in overall width and thickness, which can provide advantages of greater ease of use and comfort for patients. Such embodiments can also provide an advantage for use in infant patients, as a device that is compact in width and thickness can be easier to use effectively for attaching to the skin of smaller patients.

In certain embodiments, the thin film heater has a thickness of from about 0.2 mm to about 0.4 mm and a longest length measurement of from about 1.0 cm to about 2.0 cm. In certain embodiments, the thin film heater has a thickness of from about 0.25 mm to about 0.35 mm and a longest length measurement of from about 1.2 cm to about 1.8 cm. In certain embodiments, the thin film heater has a thickness of from about 0.28 mm to about 0.3 mm and a longest length measurement of from about 1.4 cm to about 1.6 cm. Such embodiments can provide a benefit of a temperature sensor device that uses less power than the current standard devices, due to a smaller size of the thin film heater.

In certain embodiments, the thermally conducting layer has a thickness of from about 0.5 mm to about 1.0 mm and a longest length measurement of from about 1.0 cm to about 2.0 cm. In certain embodiments, the thermally conducting layer has a thickness of from about 0.6 mm to about 0.9 mm and a longest length measurement of from about 1.2 cm to about 1.8 cm. In certain embodiments, the thermally conducting layer has a thickness of from about 0.7 mm to about 0.8 mm and a longest length measurement of from about 1.4 cm to about 1.6 cm.

In some embodiments, the skin-side thermally insulating, the medial thermally insulating and the upper thermally insulating layers form an insulating sheath having a thickness of from about 4.0 mm to about 7.0 mm and a longest length measurement of from about 2.0 cm to about 5.0 cm. In some embodiments, the skin-side thermally insulating, medial thermally insulating and the upper thermally insulating layers form an insulating sheath having a thickness of from about 4.5 mm to about 6.5 mm and a longest length measurement of from about 2.5 cm to about 4.5 cm. In some embodiments, the skin-side thermally insulating, medial thermally insulating and the upper thermally insulating layers form an insulating sheath having a thickness of from about 0.3 mm to about 1.0 mm and a longest length measurement of from about 3.0 cm to about 4.0 cm. Such embodiments can provide a benefit of a temperature sensor device that is compact in overall width and thickness, which can provide advantages of greater ease of use and comfort for patients. Such embodiments can also provide an advantage for use in infant patients, as a device that is compact in width and thickness can be easier to use effectively for attaching to the skin of smaller patients.

In certain embodiments, the temperature sensor device further includes a cable electrically connected to the sensor assembly at a distal end of the cable and to a connector at a proximal end of the cable. In certain embodiments, the cable has a thickness of from about 0.5 mm to about 1.0 mm, a width of from about 4.0 mm to about 6.0 mm, and a length of from about 80.0 cm to about 100.0 cm. In certain embodiments, the cable has a thickness of from about 0.6 mm to about 0.9 mm, a width of from about 4.3 mm to about 5.7 mm, and a length of from about 85.0 cm to about 95.0 cm. In certain embodiments, the cable has a thickness of from about 0.7 mm to about 0.8 mm, a width of from about 4.5 mm to about 5.0 mm, and a length of from about 87.0 cm to about 90.0 cm.

In some embodiments, the temperature sensor device further includes a cable electrically connected to the sensor assembly at a distal end of the cable and to a connector at a proximal end of the cable, wherein the cable is substantially round with a diameter of from about 1.5 mm to 3.0 mm. In some embodiments, the cable is substantially round with a diameter of from about 1.7 mm to 2.8 mm. In some embodiments, the cable is substantially round with a diameter of from about 2.0 mm to 2.5 mm.

In certain embodiments, the temperature sensor device further includes a battery module disposed in line with the cable. Such embodiments can provide a benefit of a power source for the temperature sensor device that is integrated into the device, so that the device does not need to use an external power source, such as a power source from an infant incubator. In some embodiments, the battery module includes a temperature control circuit electrically connected to the sensor assembly, and the battery module is electronically connected to a battery contained within the battery module. Such embodiments can provide a benefit of a control circuit that is integrated into the device, so that the device does not need to use external control circuitry, such as separate the control circuitry in an infant incubator. In certain embodiments, the battery module has a diameter of from about 2.0 cm to about 4.0 cm and a thickness of from about 4.0 mm to about 8.0 mm. In certain embodiments, the battery module has a diameter of from about 2.4 cm to about 3.6 cm and a thickness of from about 4.5 mm to about 7.5 mm. In certain embodiments, the battery module has a diameter of from about 2.8 cm to about 3.2 cm and a thickness of from about 5.0 mm to about 7.0 mm.

Embodiments of a temperature sensor device including a battery module and control circuitry can also provide benefits of being advantageous for single patient use and the use of the device as a disposable unit. Such embodiments can provide advantages of helping to prevent infection, as well as convenience in removing the need to replace batteries.

In some embodiments, the cable has a length of from about 5.0 cm to about 10.0 cm between the connector and the battery module, and a length of from about 80.0 cm to about 100.0 cm between the battery module and the sensor assembly. In some embodiments, the cable has a length of from about 6.0 cm to about 9.0 cm between the connector and the battery module, and a length of from about 85.0 cm to about 95.0 cm between the battery module and the sensor assembly. In some embodiments, the cable has a length of from about 7.0 cm to about 8.0 cm between the connector and the battery module, and a length of from about 87.0 cm to about 90.0 cm between the battery module and the sensor assembly. Such embodiments can provide advantages for use with infant patients in incubators, having cable lengths that suited to such uses.

In certain embodiments, the connector is a 2 to 21-pin connector, the battery is a lithium battery, and the temperature control circuit is a microcontroller or a servo controller.

In certain embodiments, the first skin sensor and the second skin sensor are monitored by at least one microcontroller configured to detect a failure in the first skin sensor or the second skin sensor, wherein the microcontroller is configured to send an end of life signal to a monitor if the failure is detected. In certain embodiments, the microcontroller includes a transistor switch that shorts out the thermistor for an infant incubator to induce an alarm to alert the operator that the battery is depleted, and the temperature sensor device need to be replaced.

In some aspects, a battery voltage is monitored by at least one microcontroller configured to detect a battery cutoff voltage of from about 2.2 volts to about 2.5 volts or less, and wherein the microcontroller is configured to send an end of life signal to a monitor if the battery cutoff voltage is detected. In some embodiments, the microcontroller is configured to detect a battery cutoff voltage of from about 2.3 volts to about 2.4 volts or less. In certain embodiments, the microcontroller includes series resistors to limit battery power to the heater; such embodiments can provide a benefit of protecting infant patients from burns.

In some embodiments, using a microcontroller having analog-to-digital (A/D) and digital input-output (DIO) ports can provide a benefit of combining all of the monitoring and control functions into one small programmable device. It is possible to implement these functions in discrete circuitry that monitors the temperature sensors and uses these signals to control a pulse-width modulator circuit output to the heater. Discrete circuitry can use the temperature signals to detect when a sensor fails, and actuate a transistor switch to cause the incubator to detect a failed sensor and shut down. Discrete circuitry can also monitor the battery voltage and detect a low battery condition, then actuate the transistor switch to cause the incubator to detect a failed sensor and shut down the infant warmer control.

In certain embodiments, the sensor device has a power usage of from about 2 mW to about 10 mW. In certain embodiments, the sensor device has a power usage of from about 3 mW to about 8 mW. In certain embodiments, the sensor device has a power usage of from about 4 mW to about 6 mW. Such embodiments can provide benefits of less power usage than currently available skin temperature sensor devices.

In certain embodiments, the temperature sensor device, including the sensor assembly, battery module, connector, and cables, is a single patient use device that is entirely disposable. Such embodiments can provide benefits not only of convenience, but greater patient and healthcare worker safety as a result of reducing risks of the transmission of infections.

Embodiments of Methods for Measuring Internal Body Temperature

Figure 5:
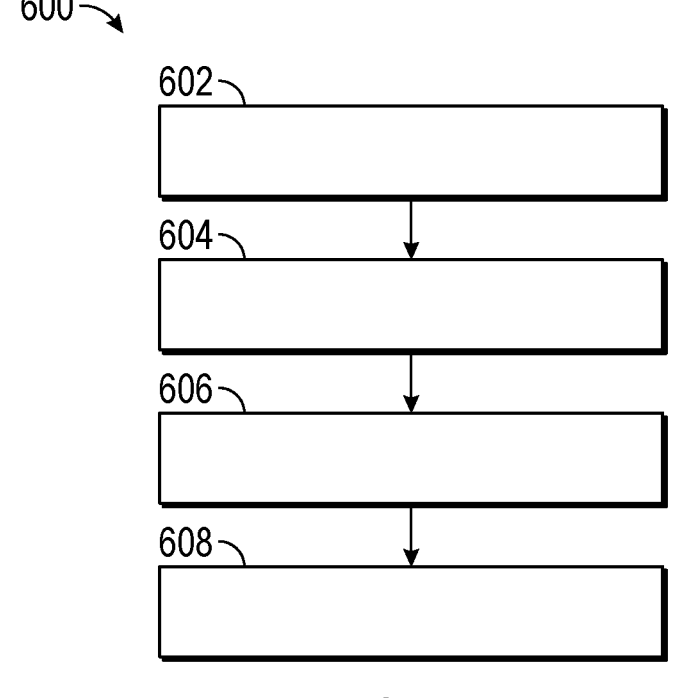
FIG. 5 shows a flow chart depicting a method for measuring the internal body temperature of a patient according to embodiments disclosed herein.

Embodiments of a method for measuring the internal body temperature of a patient are disclosed herein. As an embodiment of such a method, referring to FIG. 5, the method 600 includes: connecting a temperature sensor device to a skin area of the patient 602; connecting the temperature sensor device to an incubator 604; monitoring the internal body temperature of the patient for a duration 606, wherein the temperature sensor device comprises a gel skin adhesive layer, an electrically insulating layer, a skin-side thermally insulating layer, a sensor assembly, a thermally conductive layer, and an upper thermally insulating layer, wherein the gel skin adhesive layer is in direct contact with at least a portion of the electrically insulating layer, wherein the electrically insulating layer is in direct contact with at least a portion of the skin-side thermally insulating layer, wherein the sensor assembly comprises at least one skin temperature sensor located on a skin-facing exterior of the sensor assembly, wherein the sensor assembly comprises a thin film heater and a heater temperature sensor separated from the at least one skin temperature sensor by the thermally conducting layer, wherein the skin-side thermally insulating layer connects to the upper thermally insulating layer, surrounding the sensor assembly; and detaching and re-attaching the sensor device to the skin area of the same patient from 1 to about 5 times before disposing of the sensor device 608.

The present disclosure provides methods for measuring the internal body temperature of a patient. In some embodiments, such a method includes: connecting a temperature sensor device to a skin area of the patient, connecting the temperature sensor device to an incubator, and monitoring the internal body temperature of the patient for a duration.

In various embodiments, the temperature sensor device comprises a gel skin adhesive layer, an electrically insulating layer, a skin-side thermally insulating layer, a sensor assembly, a thermally conductive layer, and an upper thermally insulating layer; wherein the gel skin adhesive layer is in direct contact with at least a portion of the electrically insulating layer; wherein the electrically insulating layer is in direct contact with at least a portion of the skin-side thermally insulating layer; wherein the sensor assembly comprises at least one skin temperature sensor located on a skin-facing exterior of the sensor assembly; wherein the sensor assembly comprises a thin film heater and a heater temperature sensor separated from the at least one skin temperature sensor by the thermally conducting layer; and wherein the skin-side thermally insulating layer connects to the medial insulating layer which connects to the upper thermally insulating layer, surrounding the sensor assembly.

In certain embodied methods, the temperature sensor device includes a temperature control circuit electrically connected to the sensor assembly, and a first skin temperature sensor and a second skin temperature sensor in the sensor assembly. In such embodiments, the temperature control circuit senses the skin temperature with the first skin temperature sensor, powers the thin film heater in the sensor assembly to match the skin temperature, and senses the heater temperature with the second skin temperature sensor to main the thin film heater at the skin temperature.

In certain embodiments, the method further includes detaching and re-attaching the sensor device to the skin area of the same patient from 1 to about 5 times before disposing of the sensor device. In certain embodiments, the patient is an infant or a surgical patient.

EXAMPLES

Example 1—Animal Test to Demonstrate Tracking with Core Temperature

Figure 6:
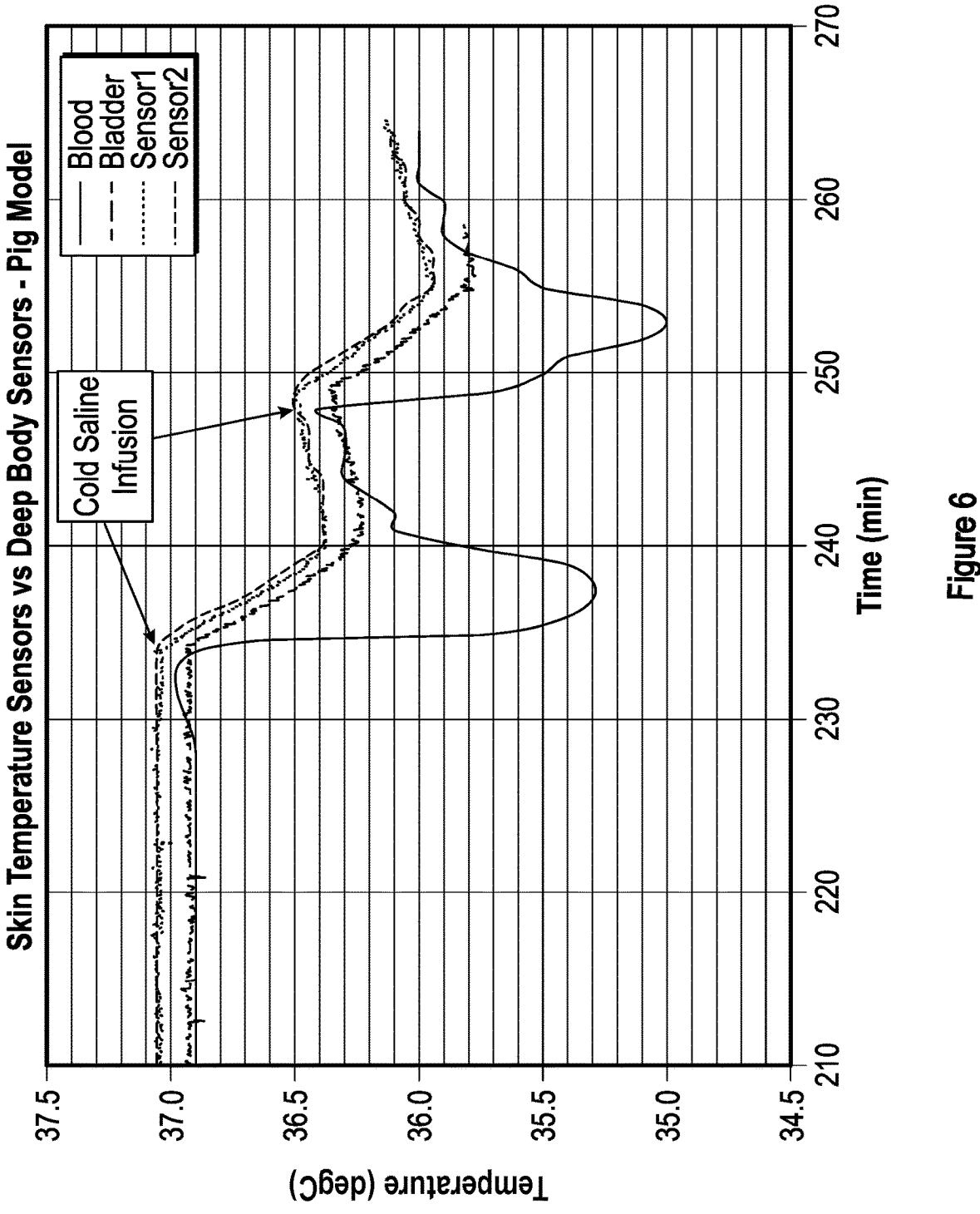
FIG. 6 shows a graph of measured animal temperature test data over time.

The capability of the temperature sensors to measure skin temperature at close correlation with deep body temperature is demonstrated in the graphs in FIG. 6, in which the outputs of two skin sensors are compared to two internal body temperature sensors, one in the bladder and one in the pulmonary artery of a sedated pig. With the pig in a supine position tilted to the right, the skin temperature sensors were placed on shaved areas with sensor 1 superior to the left shoulder at the anterior base of the neck and sensor 2 placed on the left anterior abdominal wall just superior to the hind leg. The bladder temperature was incorporated into a Foley catheter. The pulmonary artery temperature was part of a Swann-Ganz catheter. The time scale on the graph is in minutes. The temperatures were measured in a continuous manner for 210 minutes prior to data collection, with all four temperatures grouped within 36.9° C. to 37.05° C. To provide a significant core temperature change, two bags of room temperature (~17° C.) saline were infused rapidly into the pig. The first infusion occurred at minute ~234, and the blood temperature dropped from 36.9° C. to 35.3° C. at ~237 minutes and recovered back to 36.3° C. at ~242 minutes. The bladder temperature and both skin temperature sensors dropped about 0.6° C., matching the recovered blood temperature. The second bag of saline was infused at minute ~249 and the temperatures exhibited a similar 0.6° C. drop with the temperatures tracking within +/−0.1° C. after recovery of the blood temperature.

Example 2—Assembly Protocol

The completed sensor assembly shown in FIG. 3 includes all of the insulating and adhesive layers. The assembly process will begin with the core sensor assembly in FIG. 4 and add the external layers to it.

A sensor assembly as shown in FIG. 4 will be assembled per the following process.

1. The three lobed printed circuit board (438, 430 and 428) will be fabricated by a printed circuit board (PCB) vendor with the flex circuit conductor made from copper on a thin polyimide substrate. The heater element 432 will be deposited on PCB lobe 430 during the PCB fabrication process.
2. A PCB assembly vendor will prepare the PCB by applying solder paste to the conductors on the PCB. The vendor will place the electronic components, such as the temperature sensors, transistors, resistors, capacitors and microprocessor, on the PCB and solder them to the conductor pads using a standard process with a controlled temperature profile in an infrared oven.
3. The cable wires will be stripped and tinned with solder then soldered to the conductive pads on the PCB lobe 438.
4. The conductive foam layer will be adhered to the back side of PCB lobe 428 by peeling the cover from the double-sided adhesive and sticking on the PCB, while ensuring close alignment with the outline. The thin cover over the exposed backside of the double-sided adhesive on the conductive foam layer will be removed to allow boards 428 and 430 to be adhered together while ensuring close alignment of the boards.
5. The insulating foam layer 442 will be adhered to the front side of PCB lobe 430 by peeling the cover from the double-sided adhesive and sticking it on the PCB, while aligning it with the components on the PCB and the outline of the PCB. The thin cover over the exposed frontside of the double-sided adhesive on the insulating foam disk will be removed to allow board 438 to be adhered to PCB 430, while aligning the two boards.
6. Per FIG. 3, the three bottom outer layers—gel skin adhesive layer 316; electrically insulating layer 318; skin-side thermally insulating layer 320—will be adhered together into a single sheet by a converting vendor and would be die cut to size. The same converter vendor will add the medial layer 322 to complete assembly of the four layers with the gel skin adhesive layer having a protective cover on the skin side and with the medial layer having a protective cover over the topside adhesive.

7. With the cover removed from the topside adhesive on the medial layer 322, the sensor assembly 306 will be installed in the pocket in the medial layer 322, while aligning the temperature sensors 308 and 310 with the die cut openings in the insulating layer 320.
8. To complete the assembly, the cover will be peeled from the adhesive on the bottom of the insulating layer 324, and it will be aligned and placed over the medial layer 322 capturing the sensor assembly 306 inside these layers.
9. The area over the cable will be pressed together firmly to ensure that the adhesives above and below the cable make intimate contact with the cable surface to forma moisture barrier, to prevent moisture or particle ingress into the sensor assembly.
10. The sensor assembly 300 will be tested to verify performance and moved to inventory as a completed subassembly.

A battery module 108 as shown in FIG. 1 will be assembled to the sensor assembly 300 and cable 104 in the following manner:

1. Connector 106 and cable 104 will be assembled into a sub-assembly with one designated version for each model of infant incubator or warmer. The connector will be different for each model, while the cable will remain the same.
2. The battery will be mounted on a PCB to allow for connection to cable 104 from the sensor assembly 300 and for connection to cable 104.
3. The cables will be prepared for soldering to the battery PCB by stripping the insulation and tinning the lead with solder. Each cable will be soldered to the designated pads on the battery PCB.
4. The plastic battery enclosure will be designed to snap together and will have features to grip the cables inside the housing to withstand expected pull on the cable that might occur during use. The enclosure will also be designed to resist moisture ingress that might affect the interior connections.
5. The completed assembly will be tested for functionality and placed in a sealed pouch or tray. The package will be designed with a breathable film to allow for ethylene oxide sterilization.

What is claimed is:

1. A temperature sensor device for measuring the internal body temperature of a patient comprising:

a gel skin adhesive layer, an electrically insulating layer, a skin-side thermally insulating layer, a medial thermally insulating layer, a sensor assembly, a thermally conductive layer, and an upper thermally insulating layer, wherein the gel skin adhesive layer is in direct contact with at least a portion of the electrically insulating layer, wherein the electrically insulating layer is in direct contact with at least a portion of the skin-side thermally insulating layer, wherein the sensor assembly comprises at least one skin temperature sensor located on a skin-facing exterior of the sensor assembly, wherein the sensor assembly comprises a thin film heater and a heater temperature sensor separated from the at least one skin temperature sensor by the thermally conducting layer, and wherein the medial thermally insulating layer connects to the skin-side thermally insulating layer and to the upper thermally insulating layer, surrounding the sensor assembly.

2. The temperature sensor device of claim 1, wherein the gel skin adhesive layer comprises a hydrogel material, a silicone gel material, or a combination thereof; or wherein at least one skin sensor is positioned in contact with the skin-side thermally insulating layer; or wherein the medial thermally insulating layer is in direct contact with at least a portion of the skin-side thermally insulating layer and the upper thermally insulating layer.

3. The temperature sensor device of claim 1, wherein the sensor assembly further comprises a first printed circuit board and a second printed circuit board, wherein the at least one skin temperature sensor is electrically connected and mounted on a skin-side of the first printed circuit board, wherein the thin film heater and the heater temperature sensor are electrically connected to and mounted on the second printed circuit board, and wherein the first printed circuit board is connected to the second printed circuit board and the thermally conductive layer is positioned between at least a portion of the first printed circuit board and at least a portion of the second printed circuit board.

4. The temperature sensor device of claim 1, wherein the at least one skin sensor comprises a first skin sensor and a second skin sensor, and the first skin sensor is a thermistor; or wherein the heater temperature sensor comprises a thermocouple, a thermistor, a solid state sensor configured to measure temperatures from about 32° C. to about 41° C., or a combination thereof.

5. The temperature sensor device of claim 4, wherein the first skin sensor and the second skin sensor are monitored by at least one microcontroller configured to detect a failure in the first skin sensor or the second skin sensor, wherein the microcontroller is configured to send an end of life signal to a monitor if the failure is detected; or wherein a battery voltage is monitored by at least one microcontroller configured to detect a battery cutoff voltage of from about 2.2 volts to about 2.5 volts or less, and wherein the microcontroller is configured to send an end of life signal to a monitor if the battery cutoff voltage is detected.

6. The temperature sensor device of claim 1, further comprising a first circuit board, a second circuit board, and a third circuit board, wherein the first circuit board is connected to the second circuit board and the second circuit board is connected to the third circuit board, and wherein the sensor assembly further comprises a control circuit electrically connected to and mounted on the third printed circuit board, and wherein the control circuit is configured to control the temperature of the thin film heater by generating a control signal that is proportionate to a difference between a skin temperature measured by the at least one skin temperature sensor and the heater sensor.

7. The temperature sensor device of claim 1, wherein the sensor assembly has a thickness of from about 2.0 mm to about 4.0 mm and a longest length measurement of from about 1.0 cm to about 2.0 cm;

wherein the thin film heater has a thickness of from about 0.2 mm to about 0.4 mm and a longest length measurement of from about 1.0 cm to about 2.0 cm; or the thermally conducting layer has a thickness of from about 0.5 mm to about 1.0 mm and a longest length measurement of from about 1.0 cm to about 2.0 cm; or wherein the skin-side thermally insulating and the upper thermally insulating layer form an insulating sheath having a thickness of from about 4.0 mm to about 7.0 mm and a longest length measurement of from about 2.0 cm to about 5.0 cm.

8. The temperature sensor device of claim 1, further comprising a cable electrically connected to the sensor assembly at a distal end of the cable and to a connector at a proximal end of the cable, wherein the cable has a thickness of from about 0.5 mm to about 1.0 mm, a width of from about 4.0 mm to about 6.0 mm, and a length of from about 80.0 cm to about 100.0 cm; or further comprising a cable electrically connected to the sensor assembly at a distal end of the cable and to a connector at a proximal end of the cable, wherein the cable is substantially round with a diameter of about 1.5 to 3.0 mm.

9. The temperature sensor device of claim 8, further comprising a battery module disposed in line with the cable, and wherein the battery module further comprises a temperature control circuit electrically connected to the sensor assembly, and the battery module is electronically connected to a battery contained within the battery module; or the battery module has a diameter of from about 2.0 cm to about 4.0 cm and a thickness of from about 4.0 mm to about 8.0 mm; or the sensor device has a power usage of from about 2 mW to about 10 mW.

10. The temperature sensor device of claim 9, wherein the cable has a length of from about 5.0 cm to about 10.0 cm between the connector and the battery module, and a length of from about 80.0 cm to about 100.0 cm between the battery module and the sensor assembly.

11. The temperature sensor device of claim 9, wherein the connector is a 2 to 21-pin connector, the battery is a lithium battery, and the temperature control circuit is a microcontroller or a servo controller.

12. A method for measuring the internal body temperature of a patient comprising:

connecting a temperature sensor device to a skin area of the patient, connecting the temperature sensor device to an incubator, and monitoring the internal body temperature of the patient for a duration, wherein the temperature sensor device comprises a gel skin adhesive layer, an electrically insulating layer, a skin-side thermally insulating layer, a medial thermally insulating layer, a sensor assembly, a thermally conductive layer, and an upper thermally insulating layer, wherein the gel skin adhesive layer is in direct contact with at least a portion of the electrically insulating layer, wherein the electrically insulating layer is in direct contact with at least a portion of the skin-side thermally insulating layer, wherein the sensor assembly comprises at least one skin temperature sensor located on a skin-facing exterior of the sensor assembly, wherein the sensor assembly comprises a thin film heater and a heater temperature sensor separated from the at least one skin temperature sensor by the thermally conducting layer, and

wherein the medial thermally insulating layer connects to the skin-side thermally insulating layer and to the upper thermally insulating layer, surrounding the sensor assembly.

13. The method of claim 12, further comprising detaching and re-attaching the sensor device to the skin area of the same patient from 1 to about 5 times before disposing of the sensor device.

14. The method of claim 12, wherein the patient is an infant or a surgical patient.

15. The temperature sensor device of claim 3, wherein at least one of the first printed circuit board and the second printed circuit board are made of a flexible material.

16. The temperature sensor device of claim 6, wherein an interior insulating foam layer is located between at least a portion of the third printed board and a portion of the second printed board.

17. A temperature sensor device for measuring the internal body temperature of a patient comprising:

a gel skin adhesive layer, an electrically insulating layer, a skin-side thermally insulating layer, a sensor assembly, a thermally conductive layer, and an upper thermally insulating layer,

20 wherein the gel skin adhesive layer is in direct contact with at least a portion of the electrically insulating layer, wherein the electrically insulating layer is in direct contact with at least a portion of the skin-side thermally insulating layer, wherein the sensor assembly comprises at least one skin temperature sensor located on a skin-facing exterior of the sensor assembly, wherein the sensor assembly comprises a thin film heater and a heater temperature sensor separated from the at least one skin temperature sensor by the thermally conducting layer, and wherein the skin-side thermally insulating layer connects to the upper thermally insulating layer, surrounding the sensor assembly, and wherein the temperature sensor device further comprises a medial thermally insulating layer in direct contact with at least a portion of the skin-side thermally insulating layer and the upper thermally insulating layer.

* * * * *